United States Patent
Beaudry et al.

(10) Patent No.: US 11,207,355 B2
(45) Date of Patent: *Dec. 28, 2021

(54) ENRICHED MULTILAYER AMNION DERIVED TISSUE GRAFT

(71) Applicant: Amnio Technology LLC, Phoenix, AZ (US)

(72) Inventors: Christian Beaudry, Phoenix, AZ (US); Merrill B. Stromer, Phoenix, AZ (US); Grant D. Senner, Phoenix, AZ (US)

(73) Assignee: AMNIO TECHNOLOGY LLC, Phoenix, AZ (US)

( * ) Notice: Subject to any disclaimer, the term of this patent is extended or adjusted under 35 U.S.C. 154(b) by 549 days.

This patent is subject to a terminal disclaimer.

(21) Appl. No.: 15/909,857

(22) Filed: Mar. 1, 2018

(65) Prior Publication Data

US 2018/0185546 A1   Jul. 5, 2018

Related U.S. Application Data

(63) Continuation-in-part of application No. 15/542,444, filed as application No. PCT/US2015/050046 on Sep. 14, 2015, now Pat. No. 10,517,903, and a continuation-in-part of application No. 14/593,415, filed on Jan. 9, 2015, now Pat. No. 9,132,156, and a continuation-in-part of application No. PCT/US2015/019294, filed on Mar. 6, 2015, and a continuation-in-part of application No. PCT/US2015/019318, filed on Mar. 6, 2015, and a continuation-in-part of application No. PCT/US2015/019311, filed on Mar. 6, 2015, and a continuation-in-part of application No. PCT/US2015/035746, filed on Jun. 15, 2015, and a continuation-in-part of application No. 15/257,870, filed on Sep. 6, 2016, now Pat. No. 10,894,066, which is a continuation-in-part of application No. PCT/US2015/019318, filed on Mar. 6, 2015.

(60) Provisional application No. 62/465,725, filed on Mar. 1, 2017.

(51) Int. Cl.
| | |
|---|---|
| A61K 35/50 | (2015.01) |
| A61L 27/36 | (2006.01) |
| A61K 31/728 | (2006.01) |
| A61K 35/35 | (2015.01) |
| A61L 27/38 | (2006.01) |
| A61K 35/28 | (2015.01) |

(52) U.S. Cl.
CPC ............ *A61K 35/50* (2013.01); *A61K 31/728* (2013.01); *A61K 35/28* (2013.01); *A61K 35/35* (2013.01); *A61L 27/3604* (2013.01); *A61L 27/3683* (2013.01); *A61L 27/3804* (2013.01)

(58) Field of Classification Search
None
See application file for complete search history.

(56) References Cited

U.S. PATENT DOCUMENTS

| | | | | |
|---|---|---|---|---|
| 8,323,701 | B2 * | 12/2012 | Daniel | A61L 27/3604 424/583 |
| 9,132,156 | B1 * | 9/2015 | Werber | A61K 35/50 |
| 2014/0205646 | A1 * | 7/2014 | Morse | A61L 27/3687 424/423 |

FOREIGN PATENT DOCUMENTS

WO   WO 15/134946   *  9/2015   ............. A61K 38/18

OTHER PUBLICATIONS

"Coupling." Merriam-Webster.com Dictionary, Merriam-Webster, https://www.merriam-webster.com/dictionary/coupling. Accessed May 14, 2021. (Year: 2021).*
"Couple with." Merriam-Webster.com Dictionary, Merriam-Webster, https://www.merriam-webster.com/dictionary/couple%20with. Accessed May 14, 2021. (Year: 2021).*

\* cited by examiner

*Primary Examiner* — Allison M Fox
(74) *Attorney, Agent, or Firm* — Invention to Patent Services; Alex Hobson (57) ABSTRACT

An enriched amnion derived tissue graft has a stromal matrix layer and an epithelium layer. A stromal matrix layer may contain a basement membrane layer, a compact layer, a fibroblast layer, and an intermediate layer. An amnion derived tissue graft may have a plurality of tissue layers and the layers may be configured with the epithelium layers toward the inside and the stromal matrix layers toward the outside surface. An enriched portion may be coated onto or be configured within a tissue layer and have an increased concentration of cells, of proteins, growth factors, seed cells, pharmaceuticals or any combination thereof. A carrier fluid such as amniotic fluid may be used to produce an enrichment composition for coating the tissue graft. The cells within the enriched portion may be stem cells from the amnion, or cells from other tissue and may be seed cells selected based on the treatment location.

14 Claims, 10 Drawing Sheets

ENRICHED MULTILAYER AMNION DERIVED TISSUE GRAFT

CROSS REFERENCE TO RELATED APPLICATIONS

This application also claims the benefit of priority to U.S. provisional patent application No. 62/465,725, filed on Mar. 1, 2017; the entirety This application is a continuation in part of U.S. patent application Ser. No. 15/542,444, filed on Jul. 10, 2017 and currently pending, which is a U.S. national stage application of PCT application no. PCT/US15/50046 filed on filed on Nov. 14, 2015, which claims the benefit of priority to U.S. patent application Ser. No. 14/593,415, filed on Jan. 9, 2015 and issued as U.S. Pat. No. 9,132,156 on Nov. 15, 2015; and PCT application no. PCT/US15/50046 also claims the benefit of PCT/US2015/019294, PCT/US2015/019318 and PCT/US2015/01931, all filed on Mar. 6, 2015 and entitled Amnion Derived Therapeutic Compositions and Methods of Use as well as PCT/US15/35746 filed on Jun. 15, 2015. This application is also a continuation in part of U.S. patent application Ser. No. 15/257,870, filed on Sep. 6, 2016 and currently pending, which is a continuation in part of PCT/US2015/019318, having an international filing date of Mar. 6, 2015, which claims the benefit of U.S. provisional patent applications Nos. 61/949,066, and 61/949,135, both filed on Mar. 6, 2014; application Ser. No. 15/257,870 is also a continuation in part of PCT patent application no. US2015/019294, having an international filing date of Mar. 6, 2015, which claims the benefit of U.S. provisional patent applications No. 61/949,087, and 61/949,106, both filed on Mar. 6, 2014; application Ser. No. 15/257,870 is also a continuation in part of PCT patent application no. US2015/019311, having an international filing date of Mar. 6, 2015, which claims the benefit of U.S. provisional patent applications No. 61/949,087, 61/949,106, 61/949,066, and 61/949,135 all filed on Mar. 6, 2014; application Ser. No. 15/257,870 is also a continuation in part of U.S. patent application Ser. No. 14/853,889, filed on Sep. 14, 2015 and issued as U.S. Pat. No. 9,814,746 on Nov. 14, 2017, which is a continuation in part of U.S. patent application Ser. No. 14/593,415 filed on Jan. 9, 2015 and issued as U.S. Pat. No. 9,132,156, which claims the benefit of U.S. provisional patent application No. 62/012,394 filed on Jun. 15, 2014; the entirety of all applications and patents listed above are hereby incorporated by reference herein.

BACKGROUND OF THE INVENTION

Field of the Invention

The present invention relates to enriched multilayer amnion derived tissue graft.

Background

Amniotic tissue grafts utilizing amniotic materials such as an amnion layer and/or a chorion layer are used for a wide variety of treatments, including wound healing, and for intraoperative procedures, wherein the amniotic tissue graft is applied internally to an organ or a suture location to promote healing. Amniotic material aid in healing partly because they contain bioactive factors including, proteins, growth factors, cytokines, cells, and stem cells that can aid in the healing and repair of a treatment location. The concentration of the bioactive factors may vary depending on the donor and handling of the tissue.

SUMMARY OF THE INVENTION

A multilayer amnion derived therapeutic tissue graft comprises two or more tissue layers attached together and comprising at least a portion of an amnion membrane where the epithelium has been substantially preserved and chorion removed to expose the intermediate layer. In an exemplary embodiment, a tissue layer comprises the epithelium layer and a stromal matrix layer. A stromal matrix layer is a structural support layer that may include the basement membrane layer, a compact layer, a fibroblast layer, and an intermediate layer. A stromal matrix layer at least includes the basement membrane layer that is attached to the epithelium layer. An exemplary enriched multilayer amnion derived tissue graft has an enriched portion or enriched portion that includes an enrichment composition having increased concentration of proteins and/or cells, and/or growth factors, and/or cytokines and formed from a coating process of an enrichment composition. In an exemplary embodiment, proteins, such as those shown in FIGS. 17 and/or 18 may be increased to a level that is higher than that occurring in native tissue, such as about double or more, about three times or more, about five times or more, about ten times or more, about 100 times or more, about 1000 times or more or any range between and including the concentration values provided. The enrichment composition may have an increased concentration to provide a more rapid and/or more effective therapeutic effect, such as to increase the rate and effectiveness of wound healing, for example. In an exemplary embodiment, an enrichment composition and a resulting enriched portion may comprise olfactomedin 1 protein at an elevated or increased concentration as described herein. An enrichment composition and resulting enriched portion, may include, consists essentially of or consist only of amnion derived material such as amniotic fluid and/or particles produces from the amniotic membrane, for example. An enrichment composition may include non-amnion derived materials from the stromal vascular fraction and the like. An exemplary enriched multilayer amnion derived tissue graft may be placed on a treatment location to promote healing and/or rejuvenation of tissue. An exemplary enrichment composition and resulting enriched portion may be acellular comprising no viable cells and may comprise an acellular composition as described in U.S. Pat. No. 9,132,156, issued on Sep. 15, 2015, entitled Acellular Amnion Derived Therapeutic Compositions; the entirety of which is hereby incorporated by reference herein.

An exemplary enrichment composition and resulting enriched portion may comprise seed cells that are selected based on the intended use. Seed cells may be selected from the tissue that the tissue graft is targeted, such as soft tissue, organs, skin, bone and the like. The seed cells may increase the speed and effectiveness of the therapeutic effect of the tissue graft including, but not limited to, wound healing, tissue rejuvenation and the like. Seed cells may comprise stem cells including, but not limited to mesenchymal stem cells and keratinocyte stem cells. Seed cells may be incubated and expanded on a surface of a tissue layer.

An exemplary enrichment composition and resulting concentration portion may comprise a pharmaceutical compound such as an anti-inflammatory, an antimicrobial, Heprin and the like. The pharmaceutical may be a natural compound such as an extract from a plant or animal or may be synthetic.

An exemplary enriched multilayer amnion derived tissue graft comprises at least two tissue layers that are attached and may comprise, three, four or five or more layers depending on the application. An exemplary tissue layer comprises the epithelium layer and the stromal matrix layer as described herein. The layers may be attached with epithelium layer at the interface between the two tissue layers or with the stromal matrix layers at the interface between the two tissue layers. The layers may be attached by pressing, or by suturing, or by the addition of a tissue plasticizer, or chemically or solvent, or solvent mixtures, or temperature to one or more of the interface surfaces or by the application of an adhesive, such as a bio-resorbable adhesive. A cross-linking agent may be applied to one or more of the interfacing layers of the tissue layers to promote adhesion. The application of an enrichment composition to one or more of the tissue layers may improve adhesion between tissue layers. In an exemplary embodiment, an exemplary enriched multilayer amnion derived tissue graft comprises two tissue layers with the epithelium layers facing the interface. Additional example embodiments of enriched multilayer amnion derived tissue graft construction are provided herein.

Figure 1:
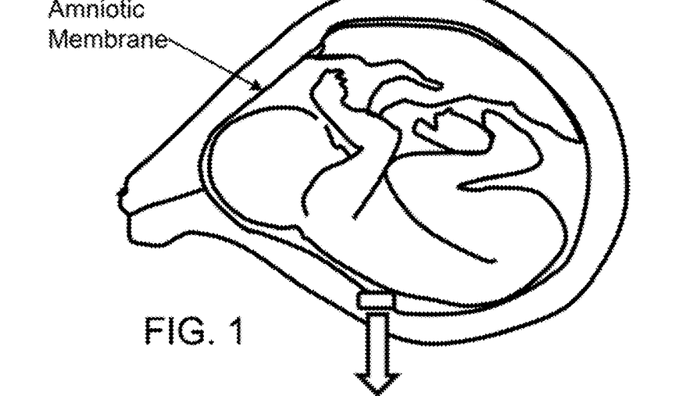
FIG. 1 shows a cross-sectional diagram of amniotic membrane surrounding a fetus in utero.

An exemplary enriched multilayer amnion derived tissue graft has an enriched portion that includes an increased concentration of cells, proteins, growth factors, and/or cytokines and formed from a coating process of an enrichment composition. An enrichment composition may include, consists essentially of, or consist only of amnion derived material such as amniotic fluid and/or particles produces from the amniotic membrane, for example. An exemplary enrichment composition consists only of amnion derived material including amniotic fluid and/or amniotic particles derived from amnion tissue, such as the amniotic membrane which includes the amnion and chorion as shown in FIG. 1. An exemplary enrichment composition consists essentially of amnion derived material when it includes amnion derived materials and a non-biological carrier such as saline, for example. An enrichment composition may comprise biological material that is non-amnion derived such as stromal vascular fraction and the like. The biological and non-amnion derived materials may include cells, proteins, growth factors and cytokines. This biological and non-amnion derived materials may be provided by a patient that is receiving an enriched multilayer amnion derived tissue graft, as described herein, as the tissue graft may be less likely to be rejected and may have better therapeutic effects when a portion is derived from the patient. It is preferred that the tissue layers and the amnion derived enrichment composition be derived from a single donor, when possible. The stromal matrix and chorion may be useful in the enrichment composition as they may protect the cells during processing and application to the tissue layer or layers. In addition, the stromal matrix and chorion also include cells, proteins, growth factors and cytokines.

As described in U.S. patent application Ser. No. 15/257,870, an enrichment composition or therapeutic composition as used therein, may comprise a mass of particles, such as amniotic membrane particles, that may be provided in a therapeutic fluid component of a therapeutic composition in any effective amount, such as more than about 1 mg/ml, more than about 5 mg/ml, more than about 10 mg/ml, more than about 50 mg/ml, more than about 100 mg/ml, more than about 500 mg/ml, and any range between and including the mass concentrations provided.

As described in U.S. patent application Ser. No. 15/257,870, the therapeutic composition, comprises a plurality of amniotic stem cells, and may comprise a high concentration, such as greater than $0.5 \times 10^6$ per milliliter of the therapeutic fluid component within the therapeutic composition. A therapeutic fluid component may also be acellular, such as an acellular amniotic fluid. An acellular amniotic fluid is described in U.S. application Ser. Nos. 14/593,415, and 14/853,889 to Amnio Technology LLC; the entirety both of which are incorporated by reference herein. A therapeutic fluid component may be referred to herein as simply a fluid component for brevity. In another embodiment, a fluid component comprises amniotic membrane that has been micronized and dispersed in a fluid. In one embodiment, a fluid component is a dispersion of micronized amniotic membrane combined with a fluid, such as plasma, saline, amniotic fluid, combinations thereof and the like. In another embodiment, a fluid component comprises a mixture of micronized amniotic membrane particles combined with an amniotic stem cell concentrated fluid. In still another embodiment, a therapeutic fluid consists essentially of a concentrated amniotic fluid wherein the quantity of amniotic stem cells is increased. The amniotic stems cells in the therapeutic composite, as described herein, may be derived from amniotic fluid and the stem cells may be concentrated by a centrifuge process. Additional fluids and agents may be added to the amniotic stem cells such as plasma, Plasma Lyte-A, from Baxter Inc., saline and the like. The concentration of cells, such as amniotic stems cells in one milliliter of a fluid component of an exemplary therapeutic composition, as described herein, may be about $0.5 \times 10^6$ or more, $1.0 \times 10^6$ or more, $5.0 \times 10^6$ or more, $10 \times 10^6$ or more and any range between and including the concentrations values provided. A high concentration of amniotic stems cells may greatly improve the effectiveness of the therapeutic composition for many applications. The therapeutic composition, as described herein, may comprise endothelial cells, mesenchymal stem cells, amniotic fluid stem cells, fibroblasts, proteins, keritinocytes, epithelial and/or epidermal cells, paratenacytes, keratinocytes, epithelial and/or epidermal cells, paratenacytes, keratinocytes and growth factors. In some embodiments, protein markers for mesenchymal stem cells may be analyzed to quantify the various types of cells within the therapeutic composition. Flow cytometry may be used to identify proteins, CD44, CD105, CD73 and CD90. In one embodiment, a therapeutic composition comprises at least 30% of mesenchymal stem cells as identified by CD73. Mesenchymal stem cells indicated by CD73 proteins may be more mobile and provide a more therapeutic effect that mesenchymal stem cells identified by the other markers. A therapeutic fluid component, as described herein, may comprise anti-inflammatory nano-particles and/or statins, HMG-CoA reductase inhibitors to reduce inflation at a treatment location.

In some embodiments, a therapeutic composition is doped with progenitor cells and the progenitor cells may be multipotent progenitor cells and/or pluripotent progenitor cells. Progenitor cells may be derived from a patient to be treated, such as from a stromal vascular fraction. Vascular fraction cells and/or progenitor cells may be included with a therapeutic composite to further improve effectiveness. Progenitor cells may be autologous or allogeneic.

In some embodiments, a therapeutic composition, or a fluid component thereof, a cellular controlled amniotic fluid therapeutic composition, is prepared by removing the cells from an amniotic fluid and then adding back in a desired concentration of these removed cells. For example, an amniotic fluid may be first filtered to remove large debris and subsequently centrifuged to separate the cells from the amniotic fluid component. The fluid component may further be processed, such as by filtration to remove any particles. In addition, the amniotic fluid component may be concentrated or diluted as desired. The amniotic fluid component may be concentrated by allowing some of the liquid to evaporate, thereby increase the concentration of growth factors and proteins within the amniotic fluid component. Conversely, the amniotic fluid component may be diluted by the addition of liquid, such as water or saline solution, for example. An exemplary therapeutic composition may be prepared by adding removed cells to the amniotic fluid component in a desired concentration, as described herein. In addition, other cells may be added to the amniotic fluid component including, stem cells from a stromal vascular fraction, bone marrow, progenitor cells and the like. These cells may be acquired from a donor that will later receive treatment utilizing the therapeutic composition.

An exemplary enrichment composition may have a controlled amount of one or more components including, but not limited to proteins and/or cells, and/or growth factors, and/or cytokines, and/or medicant agents, as generally described in U.S. patent application Ser. No. 15/257,870. A carrier fluid may be used to produce a desired concentration of components within an enrichment composition and therefor to an enriched portion of a tissue graft.

An exemplary enrichment composition comprises only fluid, such as amniotic fluid and may include a carrier fluid, such as saline.

Additional example embodiments including variations and alternative configurations of the invention are provided herein. An exemplary enrichment composition may include particles that are biological particles comprising proteins, cells, growth factors and cytokines. The particles may be microparticles having an average size of no more than about 1000 µm, no more than about 500 µm and preferably no more than 100 µm, no more than 50, no more than 25 um, no more than 10 um, no more than 5 um, no more than 1 um. Smaller particles may be preferred as they may more easily enter into apertures or recesses within a tissue layer. The particles may be separated by filtration to produce particles below a desired particle size. The particles may be produce by cryo-fracturing the biological material, wherein the tissue is frozen to about cryogenic temperatures and then fractured to make particles and preferably micro particles. The enrichment composition may act as an adhesive to bond two tissue layers together at the interface. An enrichment composition may include particles that are non-biological, such as bioresorbable material. The cells in an enrichment composition may be stem cells.

An enrichment composition may be applied to one or more tissue layers by drawing the enrichment composition though the tissue layer or layers with vacuum, or vacuum imbibing. Perforations, or apertures may be formed in a tissue layer by a chemical process, or by a physical or mechanical process. The tissue layer(s) may be perforated to form apertures to allow the enrichment composition to pass through the thickness and deposit along the apertures. Apertures may be formed by stretching the tissue, knurling the tissue, laser drilling, water jet drilling, perforated using small gauge needle, or puncturing with a physical object and the like. The apertures may be relatively small having a cross-penetration dimension of no more than about 5 mm, no more than about 2 mm, no more than 1 mm, no more than 0.5 mm no more than 0.1, and 0.01 mm smaller may be better for slower release and larger may be good for receiving larger particles and any range between and including the aperture sizes provided. Smaller apertures may allow for slower release rates, wherein the enrichment composition is delivered over a longer period of time. Larger apertures may be preferred when a shorter release time is desired. When apertures are formed in two or more tissue layers and then the enrichment composition is drawn through the two tissue layers at one time, the deposition of the enrichment composition along the apertures may act as an adhesive to attach the two layers together. This process of drawing enrichment composition through the tissue layer may be repeated to increase the deposition of the enriched portion.

An enrichment composition may be applied to a tissue layer by lyophilizing, wherein the enrichment composition is applied to a surface of the tissue layer and then the liquid portion is removed, such as through force air evaporation, vacuum, heat or any combination thereof. A flow of heated air may be passed over the surface coated with an enrichment composition and the fluid may be dried, thereby depositing an enriched portion to the tissue layer. A tissue layer may have apertures during this process and some of the enrichment composition may seep down into the apertures. In another embodiment, the tissue layer comprises recess or indentations in the surface, wherein the enrichment composition can deposit and produce pockets of enriched portions on the tissue graft surface. The pockets of the enriched portions may be discrete or there may be a surface coating of enriched portion that extends between the pockets.

The enriched portion may have an increased concentration, such as double or triple or more, of proteins, cytokines, growth factors and/or cells over the concentration of these materials in the non-enriched portion of the tissue layer.

An exemplary tissue graft and enrichment composition, as described herein, may be derived from human tissue, mammalian tissue or monotremes.

The summary of the invention is provided as a general introduction to some of the embodiments of the invention, and is not intended to be limiting. Additional example embodiments including variations and alternative configurations of the invention are provided herein. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of his specification, illustrate embodiments of the invention, and together with the description serve to explain the principles of the invention.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
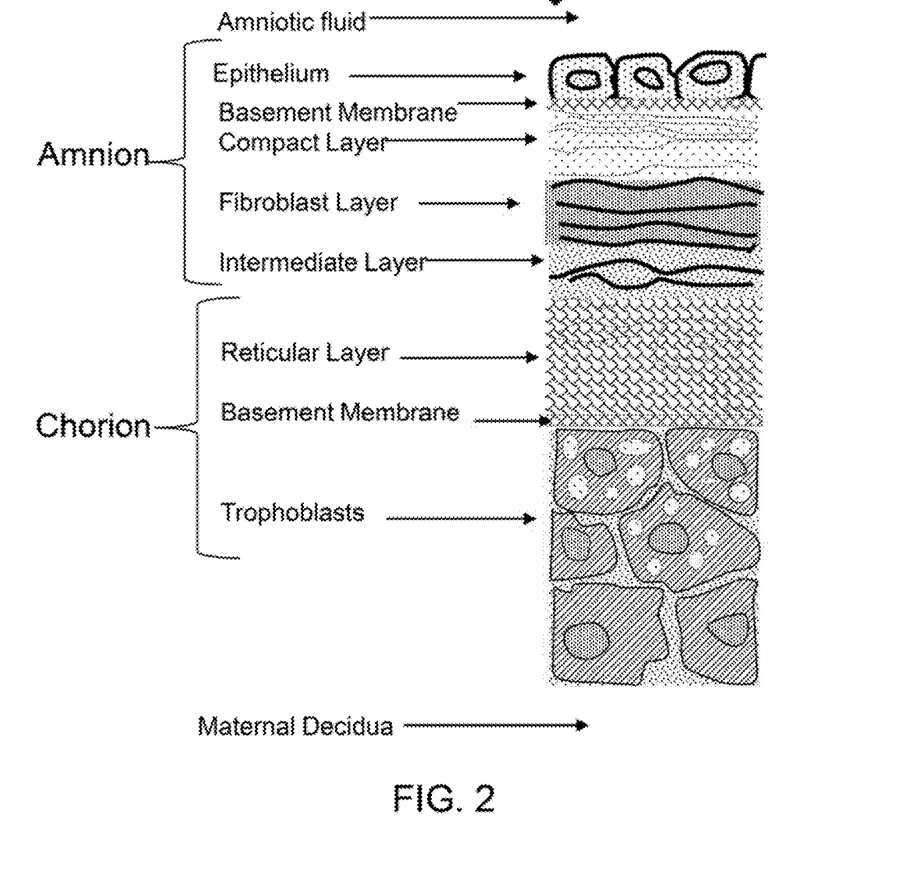
FIG. 2 shows a cross-section diagram of the layers of the amnion and chorion.

As shown if FIG. 1 the amniotic membrane surrounds a fetus in utero. As shown in FIG. 2, the amniotic membrane comprises an amnion portion and a chorion portion. As described herein, the amnion portion may be separated from the chorion. The amnion portion may be one of the plurality of tissue layers, as described herein. The amnion includes the epithelium, basement membrane, compact layer, fibroblast layer, and intermediate layer, or some portion thereof. A stromal matrix layer includes the basement membrane, compact layer, fibroblast layer, and intermediate layer or some portion thereof. The stromal matrix layer comprises proteins, growth factors and cells. The epithelium layer comprises a layer of cells. In an exemplary embodiment, a layer of the multilayer tissue graft comprises an epithelium layer and some of the components of the stromal matrix layer.

In an exemplary embodiment, the amnion, epithelium layer and/or the stromal matrix layer is used to produce an enriched portion within a multilayer tissue graft. The amnion, or a portion thereof, may be cryogenically fractured, to produce particles as described herein. The particles may consist essentially of the epithelium, consists essentially of the epithelium and base membrane, consist essentially of the epithelium, base membrane and compact layer, consist essentially of epithelium, base membrane, compact layer, and fibroblast layer, or consist essentially of epithelium, basement membrane, compact layer, fibroblast layer, and intermediate layer. The particles may micro-particles, wherein the average particle size is less than about 50 µm, and preferably less than about 25 µm. The particles may be acellular and may be place in a carrier fluid. The carrier fluid may comprise amniotic fluid or an acellular amniotic fluid.

Figure 3:
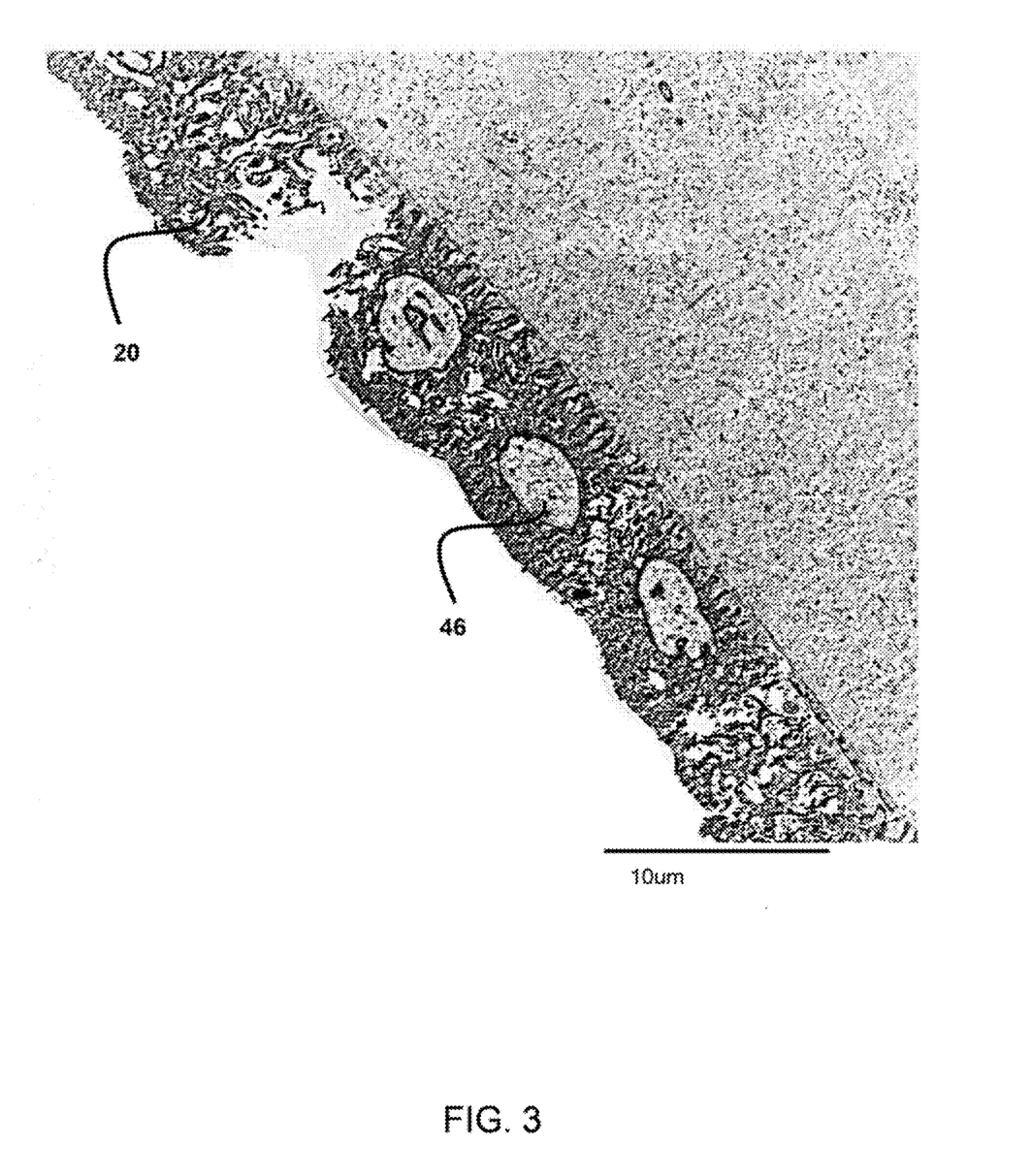
FIG. 3 shows a transmission electron micrograph (TEM) of the epithelium layer of the amniotic membrane having a single layer of epithelial cells, attached to the stromal matrix layer. The TEM is at 2500× magnification.
Figure 4:
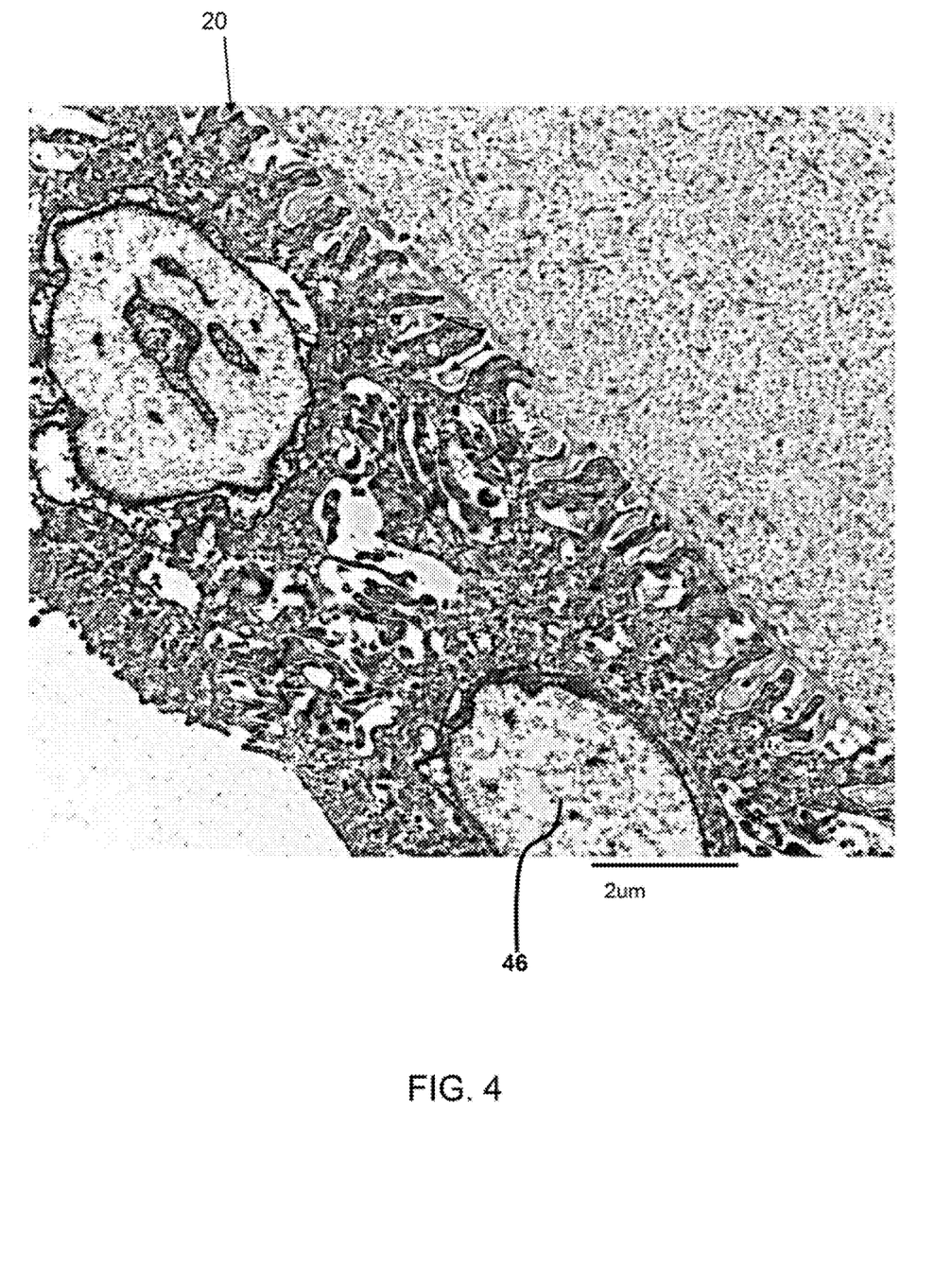
FIG. 4 shows a TEM of the epithelium layer of the amniotic membrane having a single layer of epithelial cells and attached to the stromal matrix layer. The TEM is at 8200× magnification.
Figure 5:
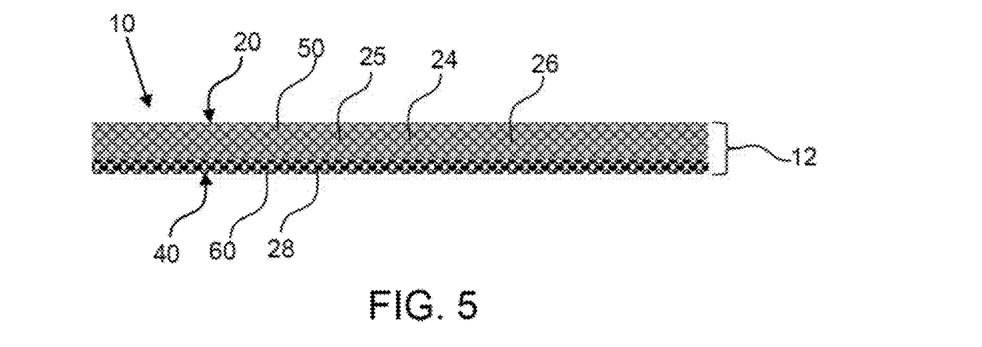
FIG. 5 shows a cross-sectional diagram of exemplary tissue layer having an epithelium layer attached to the stromal matrix layer.

As shown in FIGS. 3 and 4, the epithelium layer of the amniotic membrane 20 has a single layer of epithelial cells 46 and is attached to the basement membrane layer As shown in FIG. 5, an enriched amnion derived tissue graft 10 comprises a single tissue layer 12 of an epithelium layer 60 and a stromal matrix layer 50. The epithelium layer comprises a plurality of epithelial cells 28. The amnion derived tissue graft comprises proteins 24, growth factors 25 and cells 26. A tissue layer may comprise any portion or all of an amnion layer, as described herein.

Figure 6:
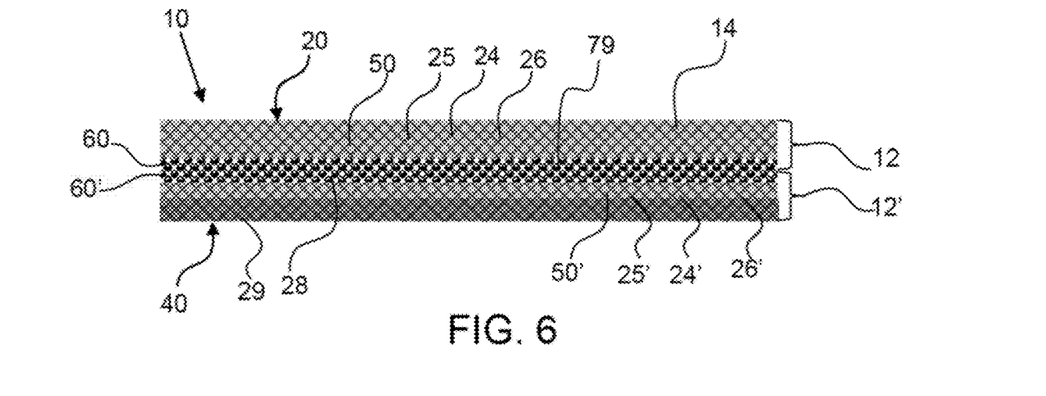
FIG. 6 shows a cross-sectional diagram of an exemplary enriched multilayer amnion derived tissue graft having two tissue layers coupled together by the epithelium layers.

As shown in FIG. 6, an enriched multilayer amnion derived tissue graft 14 comprises two tissue layers 12, 12' that are attached together by epithelium layers 60, 60'. The two stromal matrix layers 50, 50' are on the outer surfaces of the multilayer amnion derived tissue graft 14. A first stromal matrix layer 50 is on the outside surface 20 and a second stromal matrix layer 50' is on the treatment surface 40. A portion of the second stromal matrix layer has an increased concentration of proteins 24, growth factors 25 and/or cells 26 in an enriched portion 29 on the treatment surface 40. The enriched portion may improve treatment efficacy and speed of healing.

Figure 7:
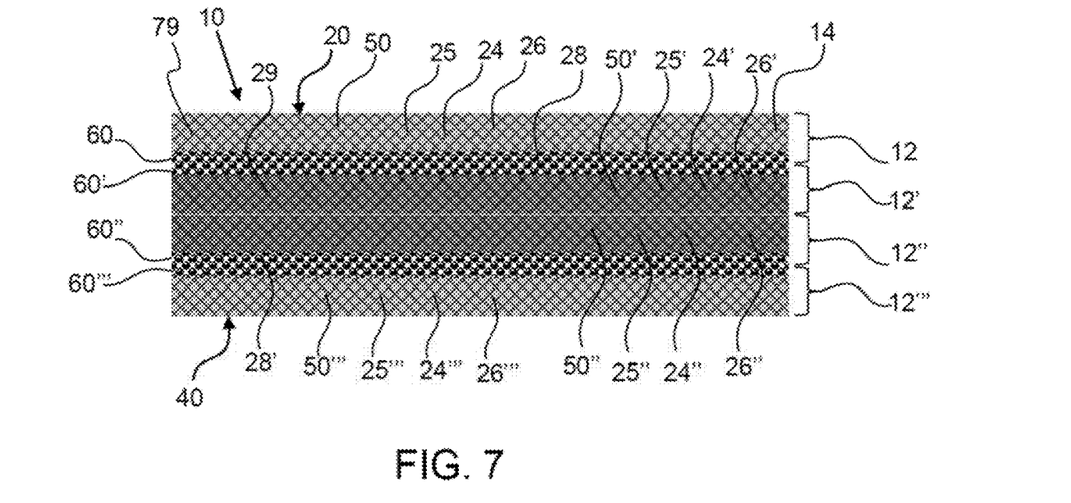
FIG. 7 shows a cross-sectional diagram of an exemplary enriched multilayer amnion derived tissue graft having four tissue layers coupled together to form said multi-layer tissue graft.

As shown in FIG. 7, an enriched multilayer amnion derived tissue graft 14 comprises four tissue layers 12 to 12''' wherein a set of tissue layers, proximal the outside surface 20, are attached together by the epithelium layers 60, 60' and a set of tissue layers, proximal the treatment surface 40, are attached together by epithelium layers 60" and 60'''. The two sets of tissue layers are attached together by the inner stromal matrix layers 50' and 50". Stromal matrix layer 50 is on the outside surface 20 and a stromal matrix layer 50''' is on the treatment surface 40. The inner stromal matrix layers 50', 50" have an increased concentration of proteins 24, growth factors 25 and/or cells 26 to create an enriched portion 29 of the enriched multilayer amnion derived tissue graft 14. This enriched portion may release the proteins 24, growth factors 25 and/or cells 26 to the treatment location to provide a "prolonged release" of these materials aid in healing.

Figure 8:
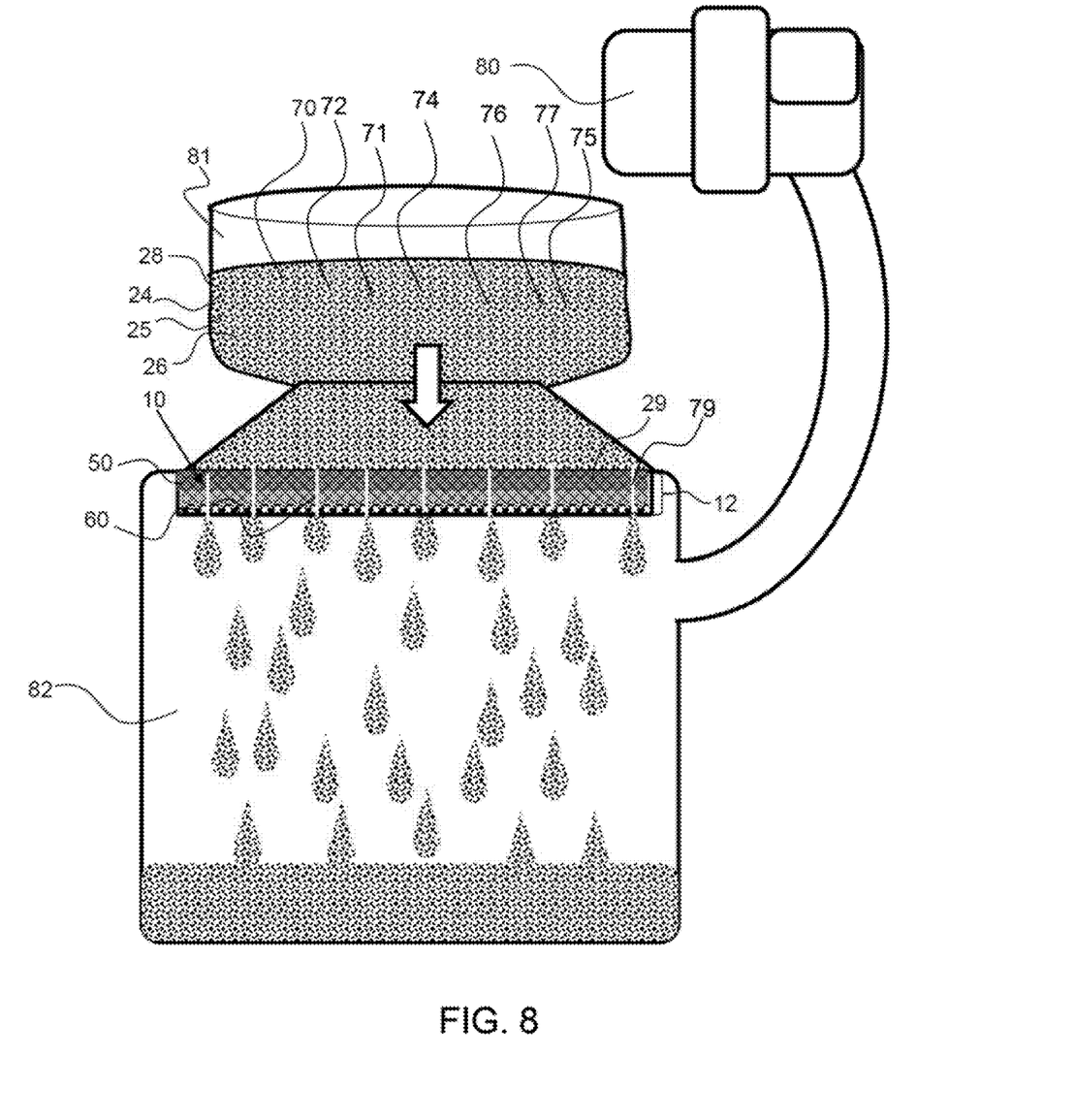
FIG. 8 shows a side view of a tissue layer treatment process wherein an enrichment composition is being drawn through apertures in the tissue layer to increase the proteins, growth factors and/or cells within the tissue layer.
Figure 9:
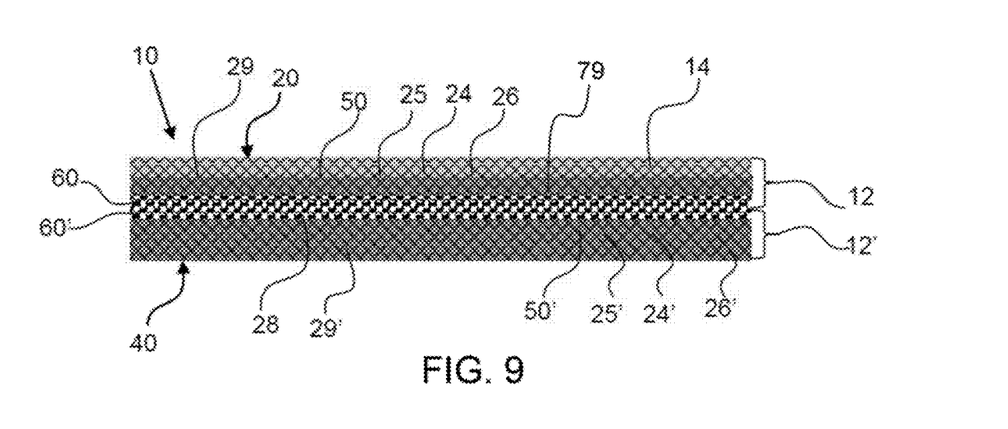
FIG. 9 shows a cross-sectional view of an exemplary enriched multilayer amnion derived tissue graft having two tissue layers and two enriched portions.

As shown in FIG. 8, a tissue layer treatment process increases the concentration of proteins 24, growth factors 25 and/or cells 26 in an enriched portion 29. An enrichment composition 70, comprises a carrier fluid 72 that may include an amnion fluid 74 and concentration particles 76, that may be derived from an amniotic material such as amnion or chorion or a non-amnion derived material, such as adipose tissue, for example, a pharmaceutical 75, seed cells 77, amnion derived cells 71 and any combination thereof. The enrichment composition 70 is being drawn through the tissue layer 12 to increase the proteins, growth factors and/or cells within the tissue layer. The amniotic fluid is drawn through the tissue layer from a reservoir 81 and into a collection container 82 by a vacuum pump 80. The amniotic fluid collected in the collection container may be introduced back into the reservoir 81 for subsequent treatment operations. This tissue layer may be combined with other tissue layers to produce an enriched multilayer amnion derived tissue graft. The tissue layer 12 may comprise a plurality of apertures 79 through the thickness of the tissue layer to allow the enrichment composition to pass therethrough. An enriched portion 29 may be within or proximal to the apertures through the thickness of the tissue layer As shown in FIG. 9, an enriched multilayer amnion derived tissue graft 14 comprises two tissue layers 12, 12'. The epithelium layers 60, 60 are facing inward, while the stromal matrix layers 50, 50' are on the outside. An enriched portion 29 is on the interior of the first tissue layer and enriched portion 29' is on the treatment surface 40 side of the second tissue layer 12'. An enriched portion may contain any of the materials in the enrichment composition as shown in FIG. 8. The enriched portion 29' may help to improve a therapeutic effect initially, with a high concentration of cells 26', proteins 24' and or growth factors 25' located on the treatment surface and enriched portion 29 may provide cells 26, proteins 24 and or growth factors 25 overtime.

Figure 10:
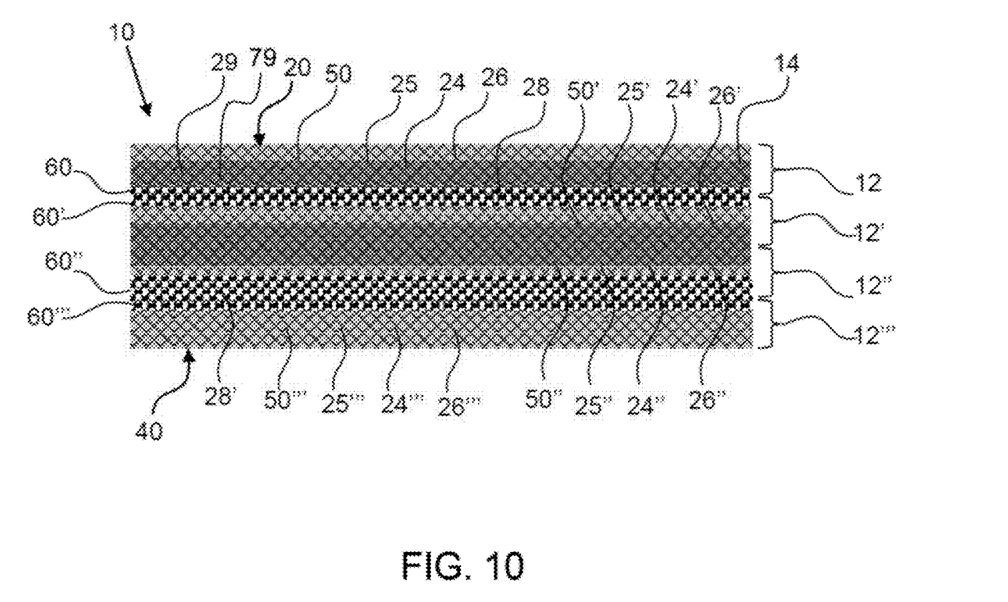
FIG. 10 shows a cross-sectional view of an exemplary enriched multilayer amnion derived tissue graft having four tissue layers.

As shown in FIG. 10, an enriched multilayer amnion derived tissue graft 14 comprises four tissue layers 12 to 12''' wherein a set of tissue layers 12, 12', proximal the outside surface 20, are attached together by the epithelium layers 60, 60' and a set of tissue layers 12" 12''', proximal the treatment surface 40, are attached together by epithelium layers 60" and 60'''. The two sets of tissue layers are attached together by the inner stromal matrix layers 50' and 50". Stromal matrix layer 50 is on the outside surface 20 and a stromal matrix layer 50''' is on the treatment surface 40. The inner stromal matrix layers 50', 50" have an increased concentration of proteins 24, growth factors 25 and/or cells 26 to create an enriched portion 29 of the enriched multilayer amnion derived tissue graft 14. This enriched portion may release the proteins 24, growth factors 25 and/or cells 26 to the treatment location to provide a "prolonged release" of these materials aid in healing. The outermost stromal matrix layer 50 also has an enriched portion 29 along the inside surface of this stromal matrix layer. The enriched portion shown in FIG. 10 may contain any of the materials in the enrichment composition as shown in FIG. 8.

Figure 11:
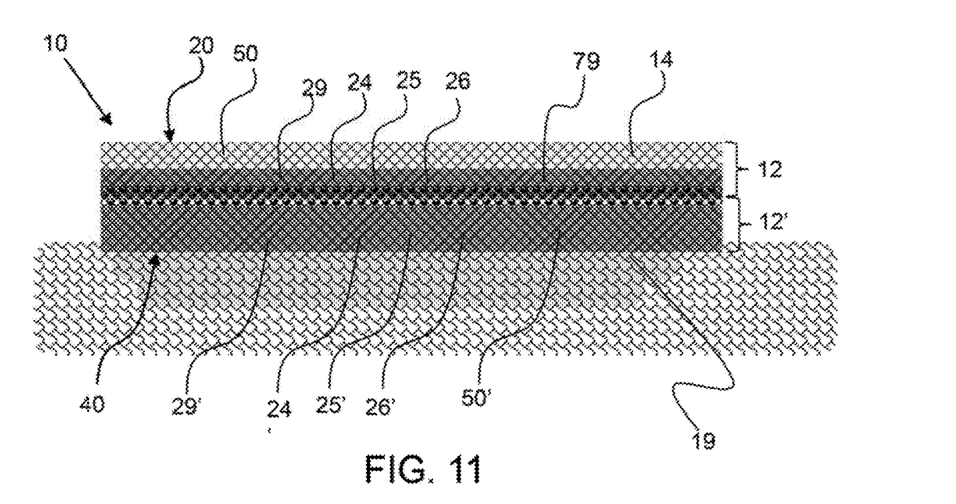
FIG. 11 shows a cross-sectional view of an exemplary enriched multilayer amnion derived tissue graft configured on a treatment location.

As shown in FIG. 11, an exemplary enriched multilayer amnion derived tissue graft 14 is configured on a treatment location 19 with an enriched portion 29 of the stromal matrix layer 50' on the treatment surface 40. The proteins 24', growth factors 25' and/or cells 26' from the enriched portion 29' have migrated into the tissue of at the treatment location to enhance healing. Another enriched portion 29 is configured at the interface between the two tissue layers and may provide cell, growth factors and proteins over time. The enriched portion may contain any of the materials in the enrichment composition as shown in FIG. 8.

Figure 12:
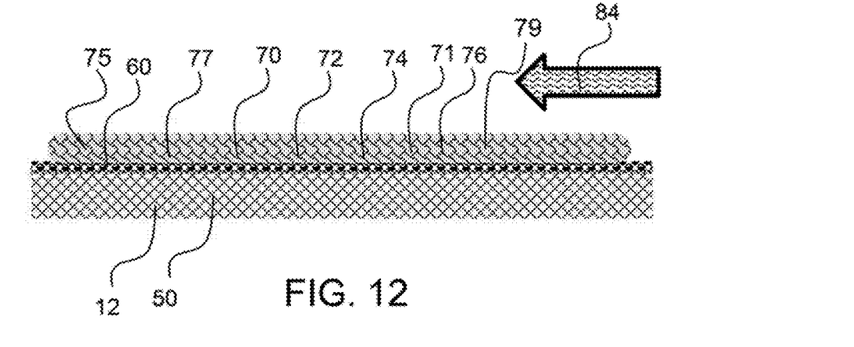
FIGS. 12 and 13 show an exemplary tissue layer being coated with an enrichment composition to form an enriched portion.
Figure 13:
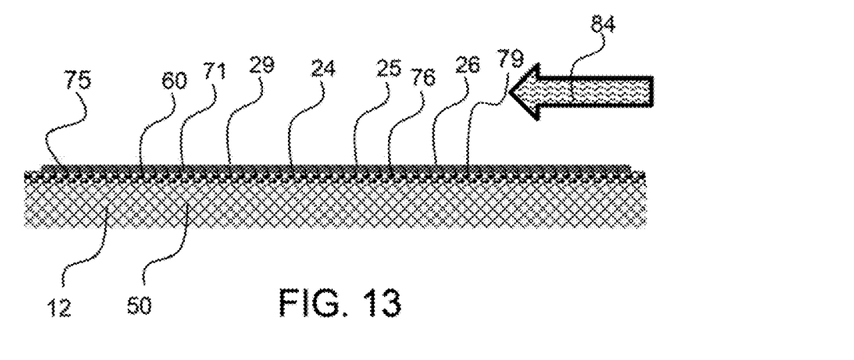

Referring to FIGS. 12 and 13, a tissue layer 12 has an enrichment composition 70 on the epithelium layer 60 and forced air 84 is driving off the moisture from the enrichment composition in FIG. 12. The enrichment composition comprises a carrier fluid 72 that may include amniotic fluid 74 and concentration particles 76 such as particles derived from amniotic tissue or other tissues, pharmaceuticals 75, seed cells 76, and amnion derived cells 71. The forced air 84 may be heated air to more quickly remove the moisture to produce the enriched portion 29 shown in FIG. 13. This process may be repeated a number of time to produce an enriched portion as desired.

Figure 14:
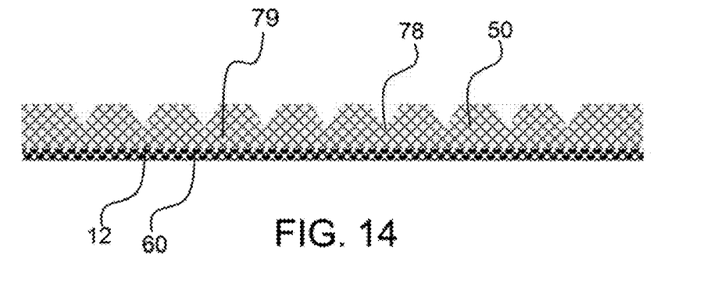
FIGS. 14 to 16 show an exemplary tissue layer having recess configured therein being coated with an enrichment composition to form an enriched portion.
Figure 15:
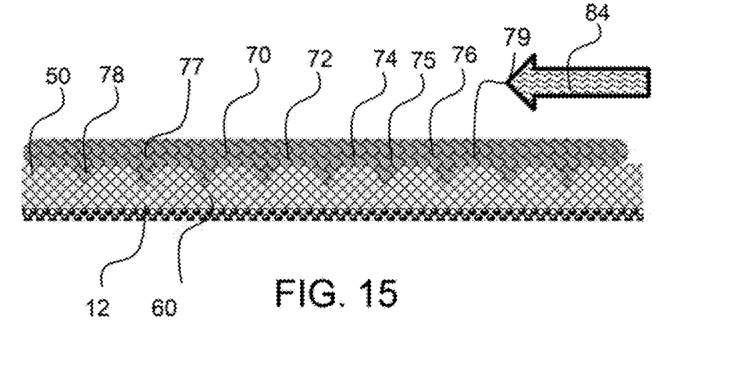
Figure 16:
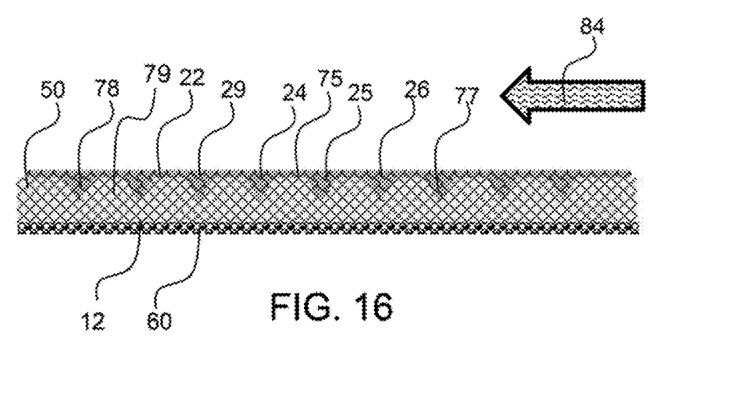

Referring to FIGS. 14 to 16, a tissue layer 12 has recesses 78 formed into the surface of the tissue layer, the stromal matrix layer in this case. The recess are indentations in the surface that may be formed by compression or by removal of a portion of the tissue layer to produce the recess. In FIG. 15, an enrichment composition has been placed on stromal matrix layer and has flowed into the recesses. Forced air flows over the tissue graft surface and drives off the liquid portion of the enrichment composition to produce an enriched portion 29 as shown in FIG. 16. The enriched portion is within the divots and forms a surface coating 22. The enrichment composition 70 and the resulting enriched portion 29 may comprise a carrier fluid 72 that may include amniotic fluid 74 and concentration particles 76 such as particles derived from amniotic tissue or other tissues, pharmaceuticals 75, seed cells 76, and amnion derived cells 71. An enriched portion may be substantially dehydrated and contain less than about 5% moisture, or in some cases less than 2% moisture.

Figure 17:
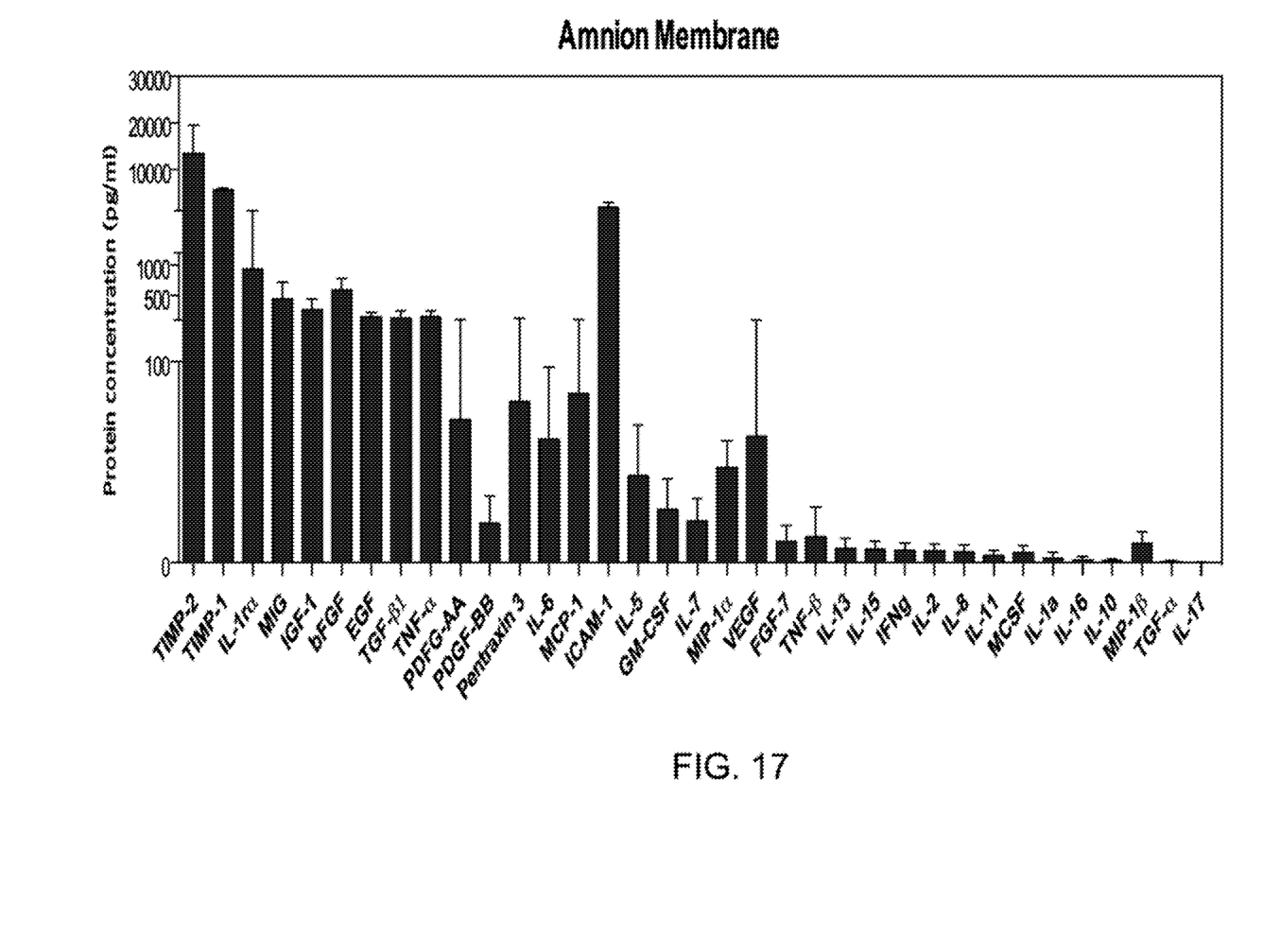
FIG. 17 shows a graph of materials, such as growth factors and cytokines, and the concentration of these materials within amnion membrane.
Figure 18:
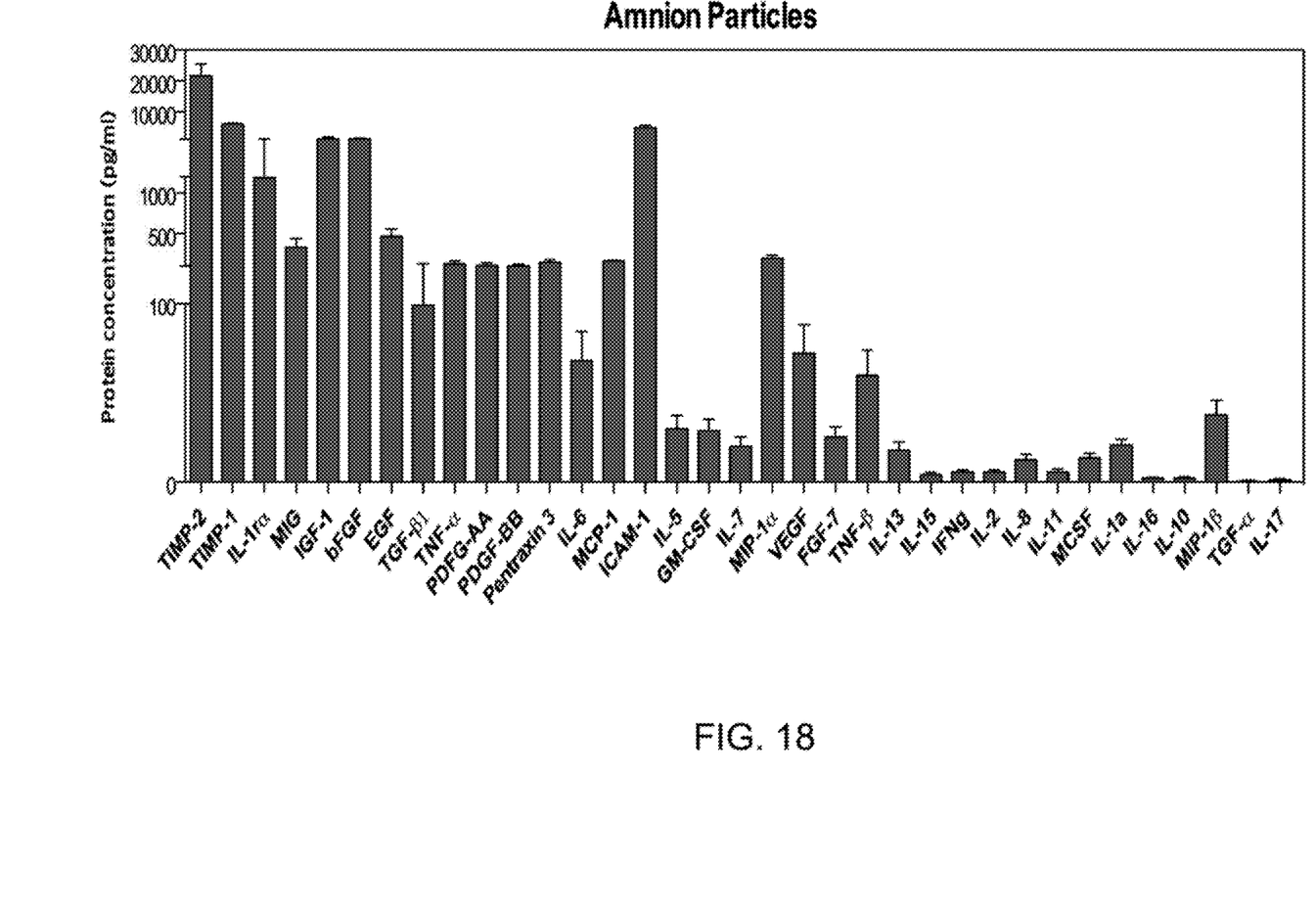
FIG. 18 shows a graph of materials, such as growth factors and cytokines, and the concentration of these materials found in amnion particles, as described herein.

FIG. 17 shows a graph of materials, such as growth factors and cytokines, and the concentration of these materials within amnion membrane.

FIG. 18 shows a graph of materials, such as growth factors and cytokines, and the concentration of these materials found in amnion particles, as described herein.

The concentration of proteins, growth factors, and cytokines can be quantified by the BCA Protein Assay, enzyme-linked immunosorbent assay (ELISA), Western Blot analysis, and the like. The concentration of proteins, and/or growth factors, and/or cytokines may be higher than the concentration in the tissue layers and may be 20% higher, 50% higher, 100% higher, five times higher, ten times higher and any range between and including the concentration ratios provided. An enriched portion may be on a treatment or outside surface, between tissue layers, or at least partially within one or more of the tissue layers, such as within a plurality of apertures or in recesses.

The present invention includes any enriched multilayer amnion derived tissue graft as described in the method claims.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An enriched multilayer amnion derived tissue graft comprising:
   a) a plurality of tissue layers having a protein concentration and comprising:
      i) a first tissue layer comprising a first amnion layer;
      ii) a second tissue layer comprising a second amnion layer;
   b) an outside surface;
   c) a treatment surface; and
   d) an enrichment composition coupled to at least one of the tissue layers to produce an enriched portion wherein the enrichment composition comprises:
      i) acellular amniotic membrane particles;
      ii) a carrier fluid; wherein the acellular amniotic membrane particles consist essentially of micronized amniotic membrane;
   wherein the carrier comprises an acellular amniotic fluid; and
   wherein the enrichment composition is essentially free of any viable amniotic membrane cells or viable amniotic fluid cells.

2. The enriched multilayer amnion derived tissue graft of claim 1, wherein the enriched portion has a protein concentration that is at least 20% higher than said protein concentration of the plurality of tissue layers.

3. The enriched multilayer amnion derived tissue graft of claim 1, wherein the enriched portion has a protein concentration that is at least twice that of said protein concentration of the plurality of tissue layers.

4. The enriched multilayer amnion derived tissue graft of claim 1, wherein the enriched portion has a protein concentration that is at least five times higher than said protein concentration of the plurality of tissue layers.

5. The enriched multilayer amnion derived tissue graft of claim 1, wherein at least one of the first or second amnion layers comprises:
   a) a stromal matrix layer; and
   b) an epithelium layer.

6. A method of making an enriched multilayer amnion derived tissue graft comprising the steps of:
   a) providing a plurality of tissue layers having a protein concentration and comprising:
      i) a first tissue layer comprising a first amnion layer;
      ii) a second tissue layer comprising a second amnion layer;
      iii) an outside surface;
      iv) a treatment surface; and
   b) providing an enrichment composition comprising;
      i) acellular amniotic membrane particles;
      ii) a carrier fluid;
   wherein the acellular amniotic membrane particles consist essentially of micronized amniotic membrane;
   wherein the carrier comprises an acellular amniotic fluid; and
   wherein the enrichment composition is essentially free of any viable amniotic membrane cells or viable amniotic fluid cells;
   c) combining the enrichment composition with at least one of tissue layers to produce an enriched portion;
   wherein the enriched portion has a protein concentration that is at least twice that of said protein concentration of the plurality of tissue layers.

7. The method of making an enriched multilayer amnion derived tissue graft of claim 6, wherein the enriched portion has a protein concentration that is at least three times higher than said protein concentration of the plurality of tissue layers.

8. The method of making an enriched multilayer amnion derived tissue graft of claim 6, wherein the enriched portion has a protein concentration that is at least twice five times that of said protein concentration of the plurality of tissue layers.

9. The method of making an enriched multilayer amnion derived tissue graft of claim 6, wherein at least one of the first or second amnion layers comprises:
   a) a stromal matrix layer; and
   b) an epithelium layer.

10. The method of making an enriched multilayer amnion derived tissue graft of claim 6, wherein the enriched portion is on the treatment surface.

11. The method of making an enriched multilayer amnion derived tissue graft of claim 6, wherein the enriched portion is between the first and second tissue layer.

12. The method of making an enriched multilayer amnion derived tissue graft of claim 6, wherein the enrichment portion has an enriched concentration of growth factors, wherein the enriched concentration of growth factors is at least double a concentration of growth factors of the plurality of tissue layers.

13. The method of making an enriched multilayer amnion derived tissue graft of claim 6, wherein the enrichment composition and the plurality of tissue layers are derived from a common donor.

14. The method of making an enriched multilayer amnion derived tissue graft of claim 6, wherein the enrichment composition is made by the process comprising the steps of:
   a) providing an amniotic membrane;
   b) micronizing said amniotic membrane to produce a plurality of micronized amniotic membrane particles having an average particle size of no more than about 100 μm;
   c) providing an amniotic fluid;
   d) decellularizing said amniotic membrane to substantially destroy any viable amniotic membrane cells to produce an acellular amniotic membrane;
   e) decellularizing said amniotic fluid to produce a decellularized amniotic fluid having no more than 500,000 intact cells per ml of said decellularized amniotic fluid; and
   f) dispersing said micronized particles into said amniotic fluid; thereby producing a therapeutic composition having essentially no viable amniotic membrane cells or viable amniotic fluid cells.

* * * * *